United States Patent
Bevot et al.

(10) Patent No.: US 8,330,470 B2
(45) Date of Patent: Dec. 11, 2012

(54) DEVICE FOR CHECKING THE OPERABILITY OF A SENSOR ELEMENT

(75) Inventors: Claudius Bevot, Stullgart (DE); Uwe Lueders, Kusterdingen-Jettenburg (DE)

(73) Assignee: Robert Bosch GmbH, Stuttgart (DE)

( * ) Notice: Subject to any disclaimer, the term of this patent is extended or adjusted under 35 U.S.C. 154(b) by 129 days.

(21) Appl. No.: 12/743,037

(22) PCT Filed: Nov. 7, 2008

(86) PCT No.: PCT/EP2008/065166
§ 371 (c)(1),
(2), (4) Date: Sep. 22, 2010

(87) PCT Pub. No.: WO2009/062896
PCT Pub. Date: May 22, 2009

(65) Prior Publication Data
US 2011/0012630 A1    Jan. 20, 2011

(30) Foreign Application Priority Data
Nov. 14, 2007  (DE) .......................... 10 2007 054 398
Feb. 26, 2008  (DE) .......................... 10 2008 011 231

(51) Int. Cl.
*G01N 27/62* (2006.01)
(52) U.S. Cl. .................. 324/465; 324/122; 324/750.02; 73/114.71
(58) Field of Classification Search .................. None
See application file for complete search history.

(56) References Cited

U.S. PATENT DOCUMENTS

| | | | |
|---|---|---|---|
| 5,298,865 A | 3/1994 | Denz et al. | |
| 5,810,997 A | 9/1998 | Okazaki et al. | |
| 6,897,661 B2 * | 5/2005 | Allen et al. | 324/663 |
| 6,912,887 B2 | 7/2005 | Ikeda | |
| 7,117,099 B2 | 10/2006 | Strassner et al. | |
| 2009/0038941 A1 | 2/2009 | Stahl et al. | |

FOREIGN PATENT DOCUMENTS

| | | |
|---|---|---|
| DE | 201 06 750 | 10/2002 |
| DE | 101 47 390 | 4/2003 |
| DE | 10 2004 042 027 | 3/2006 |
| DE | 10 2006 012 461 | 9/2007 |
| JP | S52-63155 | 11/1975 |
| JP | 02-012049 | 1/1990 |
| JP | 5107299 | 4/1993 |
| JP | 9061397 | 3/1997 |
| JP | 2003166966 | 6/2003 |

\* cited by examiner

*Primary Examiner* — Minh N Tang
(74) *Attorney, Agent, or Firm* — Merchant & Gould P.C.

(57) ABSTRACT

The invention relates to a device for checking the operability of a sensor element (100) for determining the concentration of gas components in a gas mixture, particularly of the concentration of gas components in the exhaust gas of internal combustion engine, having an external pump electrode (APE) and an internal pump and Nernst electrode (IPE), a measurement resistor (Rm) and a balancing resistor (Rtrim) connected parallel thereto being provided upstream of the external pump electrode (APE), and a pump current (Ip) being impressible into the external pump electrode by means of a pump current source, and a measuring voltage (Um) incident across the measuring resistor (Rm) via a measuring and analysis device (200) being detectable, characterized in that an activatable switch means (S) is disposed in series to the measuring resistor (Rm), which can be switched at a high impedance for a predetermined amount of time, during which the voltage across the measuring resistor is detected and analyzed in the measuring and analysis device, and that an error output occurs upon a predetermined voltage threshold value being exceeded.

3 Claims, 1 Drawing Sheet

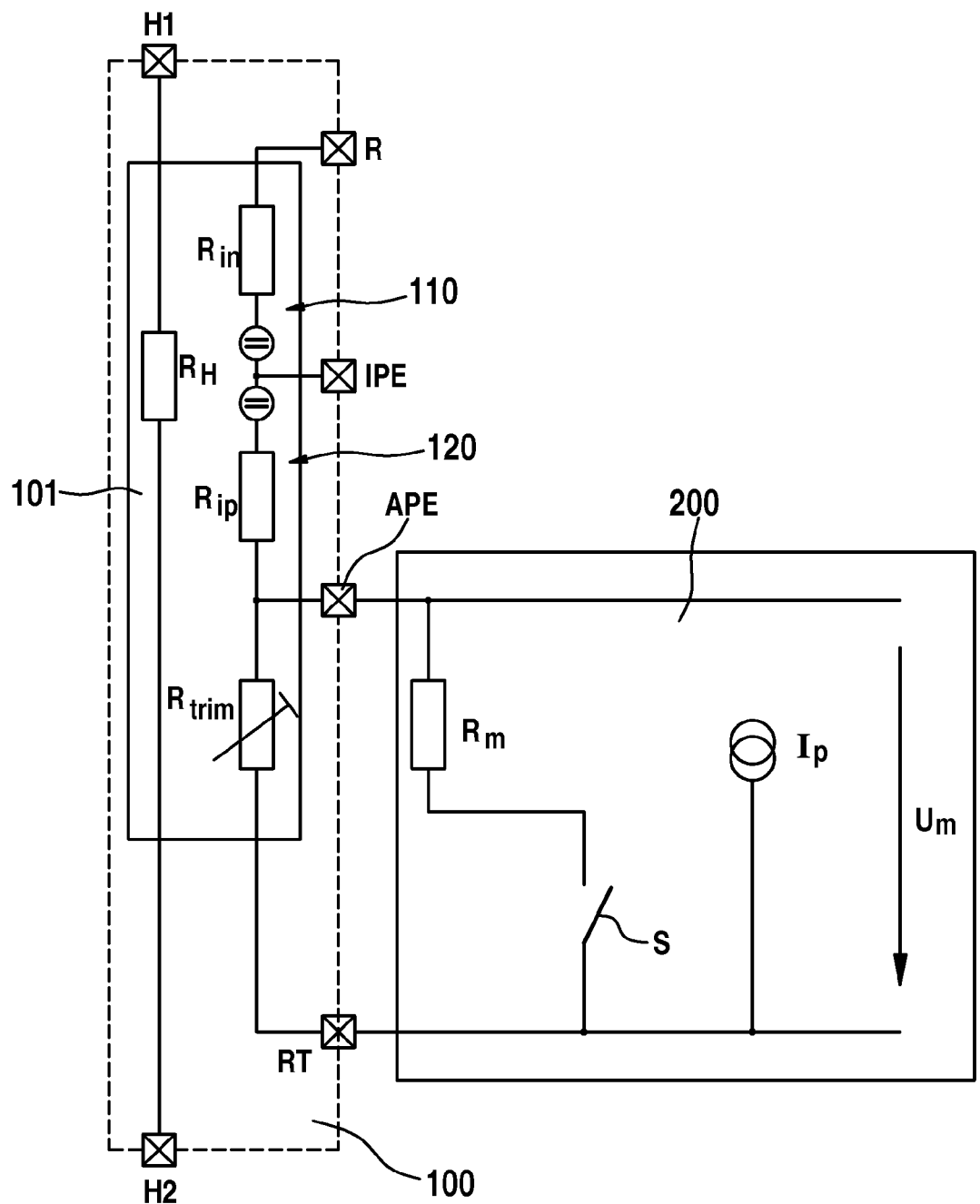

DEVICE FOR CHECKING THE OPERABILITY OF A SENSOR ELEMENT

This application is a National Stage Application of PCT/EP2008/065166, filed 7 Nov. 2008, which claims benefit of Ser. No. 10 2007 054 398.2, filed 14 Nov. 2007 in Germany and Ser. No. 10 2008 011 231.3, filed 26 Feb. 2008 in Germany and which applications are incorporated herein by reference. To the extent appropriate, a claim of priority is made to each of the above disclosed applications.

The invention relates to a method for checking the operability of a sensor element for determining the concentration of gas components in a gas mixture, particularly for determining the concentration of gas components in the exhaust gas of internal combustion engines according to the class of the independent claim 1.

BACKGROUND

Different concentration probes are known in the technical field. Besides so-called step change sensors, whose characteristic curve has a significant change at lambda=1, said change being used for determining the value lambda=1, so-called wide-band lambda probes exist. A wide-band lambda probe and a circuit arrangement for operating such a wide-band lambda probe emanate from, for example, the book publication of "Bosch Kraftfahrttechniches Taschenbuch" ("Bosch Automotive Handbook"), $25^{th}$ edition, October 2003, page 134. Such a probe as a multilayer ceramic component essentially consists of a combination of a conventional concentration probe (Nernst probe), which acts as a galvanized cell, as well as a limiting-current or "pump" cell. A voltage is applied from outside to the pump cell. If the voltage is large enough, a so-called limiting current arises, which is proportional to the difference in the oxygen concentration of both sides of the probe. Oxygen ions are transported with the current while depending on polarity. By means of the circuit arrangement, which represents an electronic closed-loop control circuit, it is assured that via a very narrow diffusion gap the concentration probe of the pump cell is always supplied with exactly that much oxygen from the exhaust gas for the condition lambda=1 to prevail at it. When there is an excess of air in the exhaust gas in the so-called lean range, oxygen is pumped out of the cell. When the residual oxygen content of the exhaust gas is too low in the rich range, oxygen is supplied to said probe by reversing the pump voltage. In so doing, the pump current forms the output signal of the probe.

The balancing of such a planar wide-band lambda probe takes place via a current divider. For this purpose, an adjustable resistor is disposed in a plug of the probe, said plug being embodied, for example, according to the German patent DE 201 06 750 U1. Said resistor is connected in parallel to a measuring resistor, which is preferably part of a control unit. In the case of diffusion barriers with a high amount of limiting current, the balancing resistor is left at low impedance. When the amount of limiting current is low, the resistance is increased as a result of a laser performing an incision into said balancing resistor. The pump current concentration characteristic curve is rotated by means of this resistor so that beside the balance point all other points also lie on the setpoint value characteristic curve.

The probe is connected via corresponding cables to an analysis circuit device, which, for example, is part of a control unit.

A line break in the feed cable to the probe can not be readily detected by sensor elements and switching devices, which are known from the technical field. According to the specifications of the On-Board Diagnostics II (OBD II), a continued monitoring of all of the emission-related components is now required. In particular lambda probes and the probe cables of such lambda probes also have to be continually monitored, for example clocked each 500 ms. At the same time, a check also must be made to determine whether a cable break exists, which can in principle occur during the operation of a motor vehicle.

Therefore, the task underlying the invention is to put forth a device for checking the operability of a sensor element, in particular a wide-band lambda probe, by which such a cable break can be detected.

SUMMARY

This task is solved by a device for checking the operability of a sensor element of the generic type through the characteristics of claim 1. It is the basic idea of the invention to detect a drop in load at a connecting sensor element without a plausibility check of probe signals having to be done. Said signals can also not be unambiguous when a sudden change in state occurs.

For this reason, the invention provides for an activatable switch means to be disposed in series to the measuring resistor, which can be switched at a high impedance for a predetermined amount of time, during which the voltage across the measuring resistor is detected and analyzed in the measuring and analysis device, and for an error output to occur upon a predetermined voltage threshold value being exceeded. The measuring resistor is effectively switched off by this switch means, and this action also thereby prevents a current from continuing to flow into the probe when a cable break occurs. This is the case because the measuring resistor has essentially the same value as the balancing resistor.

An advantageous embodiment thus provides for the switch means to be a semiconductor switch, in particular a transistor, which can be activated in a simple manner. Provision can furthermore be made in an advantageous manner to implement this semiconductor as a part of an integrated circuit, which can, for example, be a part of a control unit.

BRIEF DESCRIPTION OF THE DRAWINGS

An example of embodiment of the invention is depicted in FIG. 1 of the drawing and is explained in detail in the following description.

DETAILED DESCRIPTION

A device for checking the operability of a sensor element for determining the concentration of gas components in a gas mixture, particularly the concentration of gas components in the exhaust gas mixture of internal combustion engines, is schematically depicted in the figure. The sensor element 100 has a Nernst cell 110 and a pump cell 120. The Nernst cell and the pump cell are in each case represented by their equivalent circuit diagram in FIG. 1, the Nernst cell by a voltage source and the internal resistor $R_{iN}$, the pump cell by a voltage source and the internal resistor $R_{iP}$. The wide-band lambda probe additionally has a heater, which is schematically depicted by the resistor $R_H$. The probe is heated up by this heater until a temperature is achieved, which allows for a proper operation of the probe. The actual probe 101 is disposed in a housing, which has connector pins H1, H2 for the heater and connector pins R as well as IPE for the Nernst cell as well as connector pins APE, IPE for the pump cell. The Nernst electrode and the electrode of the internal pump electrode are identical. The sensor element additionally has a trimming resistor $R_{trim}$, which is disposed between the connection of the outer pump electrode APE and a probe pin RT.

The balancing resistor $R_{trim}$ with a measuring resistor $R_m$ forms a current divider, through which the balancing of the characteristic curve of the wide-band lambda probe takes place. The adjustable resistor $R_{trim}$ is preferably disposed in a plug of the probe. In the case, for example, of diffusion barriers with a high amount of limiting current, the balancing resistor $R_{trim}$ is left at a low impedance. On the other hand in the case of a low amount of limiting current, a laser incision is introduced into the balancing resistor $R_{trim}$ in an inherently known manner, which increases the resistance value. In this way the characteristic curve can be rotated in an inherently known manner so that beside the balancing point, all other points also lie on the setpoint characteristic curve. In the case of such a probe, a current (pump current $I_p$, depicted in FIG. 1 as pump current source) is impressed into the pump cell via the probe pin RT up until the Nernst voltage arises in the Nernst cell. The probe pin RT is connected to a lambda probe measuring and analysis device 200. The corrected current $I_p$ is a measurement for the composition of the exhaust gas/air mixture. The current thereby flows across the balancing resistor $R_{trim}$ into the probe 100 as well as across the measuring resistor $R_m$ of the measuring and analysis device 200, which is connected in parallel thereto. The drop in voltage $U_m$ across the measuring resistor $R_m$ is analyzed for measuring the air ratio, i.e. the lambda value.

If a cable break occurs now, for example a break in the probe cable at the probe pin RT, the measuring resistance $R_m$ is then further maintained in the measuring and analyzing device 200, which is, for example, a part of a control unit; and the current can continue to flow. As the value of the balancing resistance $R_{trim}$ lies in the same range as the value of the measuring resistance $R_m$, the absence of the balancing resistance $R_m$ is not unambiguously suggested in this instance and therefore neither is a cable break. In order to be able to unambiguously detect a cable break, provision is therefore made in the invention for the measuring resistor $R_m$ to be switched off via a low resistance switch S. For this purpose, the switch S, which is connected in series to the measuring resistor $R_m$, is switched at a high impedance. If the attempt is made in this instance to continue to impress a current when the balancing resistance $R_{trim}$ is absent due to a line break, the voltage will continue to increase at the probe pin RT until a threshold is exceeded. Said threshold would not be achieved, respectively exceeded, without a drop in load. A drop in load can accordingly be unambiguously suggested by a measurement of the voltage.

In order to determine whether a drop in load is suggested at the probe pin RT, the switch S is thus switched at a high impedance for a predetermined amount of time and the measuring voltage $U_m$ is detected in combination in said amount of time. If said measuring voltage $U_m$ approaches a limit value and if it exceeds a predetermined threshold value, a drop in load is suggested.

It is to be noted that the switch S can be a semiconductor switch, which, for example, can be implemented using a transistor. The transistor can thereby be a transistor of an integrated circuit, which in turn can be a part of the circuit arrangement 200 and particularly a part of an engine control unit.

The invention claimed is:

1. Device for checking the operability of a sensor element for determining the concentration of gas components in a gas mixture, particularly the concentration of gas components in the exhaust gas of internal combustion engines, having a first external pump electrode and an internal pump and Nernst electrode, a measuring resistor and a balancing resistor connected parallel thereto being provided between the external electrode and a probe pin, and a pump current being impressible into the external pump electrode by means of a pump current source, and a measuring voltage incident between the external electrode and the probe pin being detectable via a measuring and analysis device wherein an activatable switch means is disposed in series to the measuring resistor, which can be switched at a high impedance for a predetermined amount of time, during which the voltage across the measuring resistor is detected and analyzed in the measuring and analysis device, and that an error output occurs upon a predetermined voltage threshold value being exceeded.

2. Device according to claim 1, wherein the switch means is a semiconductor, in particular a transistor.

3. Device according to claim 2, wherein the semiconductor is part of an integrated circuit.

\* \* \* \* \*

UNITED STATES PATENT AND TRADEMARK OFFICE
CERTIFICATE OF CORRECTION

PATENT NO. : 8,330,470 B2  
APPLICATION NO. : 12/743037  
DATED : December 11, 2012  
INVENTOR(S) : Bevot et al.

Page 1 of 1

It is certified that error appears in the above-identified patent and that said Letters Patent is hereby corrected as shown below:

On the title page, item (75) Inventors: "Stullgart (DE);" should read --Stuttgart (DE);--

Signed and Sealed this  
Sixteenth Day of July, 2013

Teresa Stanek Rea  
*Acting Director of the United States Patent and Trademark Office*